United States Patent
Ebert et al.

(10) Patent No.: US 11,168,048 B2
(45) Date of Patent: Nov. 9, 2021

(54) ALKOXYLATION OF HYDROXY ACIDS

(71) Applicant: BASF SE, Ludwigshafen am Rhein (DE)

(72) Inventors: Sophia Ebert, Ludwigshafen (DE); Roman Benedikt Raether, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/625,991

(22) PCT Filed: Jun. 25, 2018

(86) PCT No.: PCT/EP2018/066925
§ 371 (c)(1),
(2) Date: Dec. 23, 2019

(87) PCT Pub. No.: WO2019/002189
PCT Pub. Date: Jan. 3, 2019

(65) Prior Publication Data
US 2020/0165184 A1 May 28, 2020

(30) Foreign Application Priority Data
Jun. 26, 2017 (EP) ..................... 17177850

(51) Int. Cl.
*C07C 51/367* (2006.01)
*C07C 59/125* (2006.01)

(52) U.S. Cl.
CPC .......... *C07C 51/367* (2013.01); *C07C 59/125* (2013.01)

(58) Field of Classification Search
CPC ..... C07C 51/373; C07C 59/125; C07C 59/58; C07C 51/367; C11D 3/2086; C11D 3/2089
See application file for complete search history.

(56) References Cited

U.S. PATENT DOCUMENTS

| 3,799,977 | A | * | 3/1974 | Rutledge et al. ....... C07C 59/06 562/537 |
| 4,237,253 | A | | 12/1980 | Jacquet et al. |
| 4,366,151 | A | | 12/1982 | Krapf et al. |
| 4,814,101 | A | | 3/1989 | Busch et al. |
| 5,880,252 | A | | 3/1999 | Breitenbach et al. |
| 9,826,734 | B2 | | 11/2017 | Hofmann et al. |

FOREIGN PATENT DOCUMENTS

| CN | 101230464 A | 7/2008 |
| CN | 102850538 A | 1/2013 |
| CN | 105669914 A | 6/2016 |
| DE | 740366 | * 5/1943 |
| DE | 2150557 A1 | 6/1972 |
| DE | 2817369 A1 | 10/1978 |
| DE | 3708451 A1 | 10/1988 |
| DE | 3929973 A1 | 3/1991 |
| DE | 4333238 A1 | 4/1995 |
| EP | 0017059 A1 | 10/1980 |
| GB | 1368495 A | 9/1974 |
| JP | 2003064286 A | 3/2003 |
| JP | 2013181006 A | 9/2013 |
| WO | 2008/015381 A1 | 2/2008 |
| WO | 2013/014126 A1 | 1/2013 |
| WO | 2017037188 A1 | 3/2017 |

OTHER PUBLICATIONS

DE740366 translated (Year: 1943).*
Lochee et al. (Biodegradable poly(ester-ether)s: ring-opening polymerization of D,L-3-methyl-1,4-dioxan-2-one using various initiator systems, Polym Int; 59: 1310-1318, Published Jun. 2010) (Year: 2010).*
STN 11 1984 one page (Year: 1984).*
Inokuma et al. (Active transport of alkali and alkaline earth metal cations by oligo(oxyethylene) alkyl ethers bearing a carboxyl group, Yukagaku, 37 (4) pp. 287-290, published 1988). (Year: 1988).*
Inokuma et al. translation (Year: 1988).*
Database Registry [online], Chemical Abstracts Service, Columbus, Ohio, US (May 14, 2014); XP002774811. 1 page.
Database Registry [online], Chemical Abstracts Service, Columbus, Ohio, US (May 14, 2014); XP002774812. 1 page.
English Translation of the International Preliminary Report on Patentability for International Patent Application No. PCT/EP2018/066925, dated Jun. 5, 2019, 6 pages.
International Search Report for International Application No. PCT/EP2018/066925 dated Sep. 26, 2018; 5 pages.

\* cited by examiner

*Primary Examiner* — Yevgeny Valenrod
*Assistant Examiner* — Blaine G Doletski
(74) *Attorney, Agent, or Firm* — Armstrong Teasdale LLP

(57) ABSTRACT

Alkoxylated hydroxycarboxylic acids according to a formula I' are provided herein, as well as uses thereof and a process for production thereof.

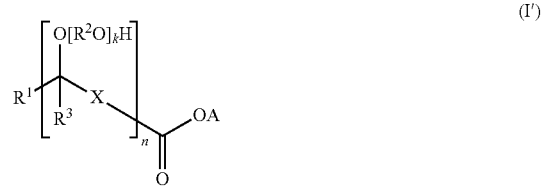

(I')

Compound 2-[2-(2-hydroxyethoxy)ethoxy]propanoic acid being exclude.

17 Claims, No Drawings

ALKOXYLATION OF HYDROXY ACIDS

CROSS-REFERENCE TO RELATED APPLICATIONS

This application is a U.S. National Phase application of PCT/EP2018/066925, filed Jun. 25, 2018, which claims the benefit of priority to EP Application No. 17177850.9, filed Jun. 26, 2017, the contents of which are hereby expressly incorporated by reference in their entirety.

BACKGROUND OF THE INVENTION

The present invention relates to alkoxylated hydroxycarboxylic acids, use thereof and a process for production thereof.

PRIOR ART

Surfactants are among the most widely used compounds exhibiting activity at interfaces, and are found in many different applications not only in detergents and cleaners but also in the field of cosmetics. The conventional surfactants used especially in cosmetics are alkoxylated hydroxycarboxylic acids (alkoxylated hydroxyacids). To the extent that the carboxylic acid group(s) has/have not already been esterified, the alcohol groups and the carboxylic acid groups undergo the same reaction during alkoxylation. The resultant esters and ethers feature good foaming properties, high cleaning power, and low sensitivity to hardness and growth, and are widely used for the production of cosmetic products such as hair shampoos, bubble baths and shower gels, and are also used in hand-dishwashing compositions.

Ethercarboxylates are known anionic surfactants. They are obtained from the corresponding alcoholethoxylates via reaction with chloroacetic acid. This synthesis has the disadvantage of producing a large quantity of sodium chloride.

Many current applications place requirements on surfactants that go beyond good activity at interfaces. A particular requirement in cosmetics is high dermatological compatibility. Other properties generally desired are adequate water-solubility, good compatibility with as many as possible of the active ingredients and auxiliaries used in cosmetics, good foaming properties and good rheology. There is moreover a need for surfactants which can be produced at least to some extent from biogenic sources and especially also from renewable raw materials. There is also a need for surfactants which on the one hand have free carboxylic acid groups, i.e. highly hydrophilic groups, and on the other hand have groups with dispersing activity, especially oligo- and poly-alkylene oxide groups. There is therefore a particular need for selective alkoxylation reactions of hydroxycarboxylic acids with retention of the acid function.

Alkoxylation reactions of hydroxycarboxylic acids have been known for a long time.

CN 102850538 describes polylactic acid of which the hydroxy groups are not lactic-acid-terminated, and the process for producing same. The process permits termination via addition of an endcapper during or after polylactic-acid polymerization in a melt- or solid-phase polymerization process.

WO 2013/014126 describes etherified lactate esters and use of these in crop-protection agents. That document does not describe alkoxylated free polylactic acids.

EP 0017059 describes the alkoxylation of carboxylic acids with additionally their one or more hydroxy groups. Monohydroxy fatty acids are reactive with ethylene oxide. However, this reaction is not selective. An esterification reaction takes place alongside the alkoxylation of the carboxylic acid function. The hydroxy groups are moreover likewise alkoxylated. The resultant products have a very low acid number of less than 5 mg KOH/g. In contrast, the resultant esters have a high saponification value, depending on the degree of alkoxylation.

WO 2008/015381 describes surface cleaning compositions. Among compounds disclosed are those of formula $R_1(OC_2H_4)_n$—$OCH_2COO^-M^+$, where $R_1$ is a $C_4$-$C_{18}$-alkyl; these compounds, then, are capped on the hydroxy terminus.

It has not hitherto been possible to alkoxylate hydroxycarboxylic acids selectively. The hydroxy functions are also alkoxylated alongside the preferred alkoxylation of the acid function. Transesterification reactions moreover occur. A complex product mixture is therefore obtained.

The present invention is based on the object of providing novel compounds which have advantageous suitability as compounds with activity at interfaces for various applications. They are especially intended to be suitable for covering a complex range of requirements which has been described in the introduction. In particular, an intention is to provide a process which permits selective alkoxylation of hydroxycarboxylic acids with retention of the acid function.

Surprisingly, it has now been found that this object is achieved via the compounds of the invention and the process of the invention.

SUMMARY OF THE INVENTION

The invention firstly provides compounds of the general formula (I)

$$R-C(=O)-O-A \qquad (I)$$

in which
R is an organic moiety which bears at least one —O—[$R^2$—O]$_k$—H substituent; in which
$R^2$ is —$CR^aR^b$—$CR^cR^d$—, in which each $R^a$, $R^b$, $R^c$ and $R^d$ is mutually independently selected from hydrogen, unsubstituted $C_1$-$C_{20}$-alkyl and unsubstituted $C_5$-$C_7$-cycloalkyl and $C_5$-$C_7$-cycloalkyl which bears 1, 2 or 3 substituents mutually independently selected from $C_1$-$C_6$-alkyl and $C_2$-$C_6$-alkenyl,
where two moieties $R^a$ and $R^c$, together with the —$CR^b$—$CR^d$— group to which they are bonded, can also be $C_5$-$C_7$-cycloalkyl which is unsubstituted or which bears 1, 2 or 3 substituents mutually independently selected from $C_1$-$C_6$-alkyl and $C_2$-$C_6$-alkenyl; and
k is a number from 1 to 100; and
A is hydrogen or one cation equivalent.

The compound 2-[2-(2-hydroxyethoxy)ethoxy]propanoic acid (CAS 1604403-13-5 (S), 1604453-64-6 (R)) is excluded from the compounds of the general formula (I).

A preferred embodiment is provided by compounds of the formula (I')

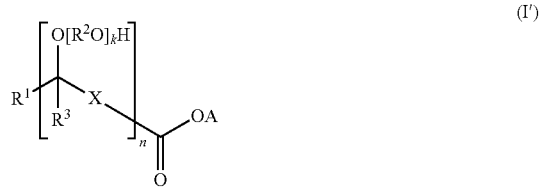

(I')

in which
$R^1$ is selected from hydrogen, a linear or branched saturated or unsaturated aliphatic hydrocarbon moiety having from 1 to 30 carbon atoms, saturated or unsaturated cycloaliphatic hydrocarbon moieties having from 3 to 10 carbon atoms and aryl,
$R^3$ is selected from hydrogen and methyl,
X is respectively a bond or a divalent linear or branched saturated or unsaturated aliphatic hydrocarbon moiety having from 1 to 30 carbon atoms, or a divalent saturated or unsaturated cycloaliphatic hydrocarbon moiety having from 3 to 10 carbon atoms;
n is a number from 1 to 10; and
A, $R^2$ and k respectively independently are defined as above or below.

The invention further provides a process for the production of compounds of the general formula (I), where
a) at least one hydroxycarboxylic salt of the general formula (III)

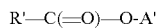
R'—C(=O)—O-A'    (III)

in which
R' is an organic moiety which bears at least one hydroxy group and in which all of the optionally comprised acid groups have been fully deprotonated; and
each A' is respectively independently one cation equivalent;
is reacted with at least one epoxide of the general formula (IV)

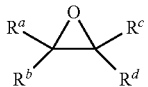
(IV)

in which
each $R^a$, $R^b$, $R^c$ and $R^d$ is mutually independently selected from hydrogen, unsubstituted $C_1$-$C_{20}$-alkyl and unsubstituted $C_5$-$C_7$-cycloalkyl and $C_5$-$C_7$-cycloalkyl which bears 1, 2 or 3 substituents which are mutually independently selected from $C_1$-$C_6$-alkyl and $C_2$-$C_6$-alkenyl,
where two moieties $R^a$ and $R^c$, together with the —$CR^b$—$CR^d$— group to which they are bonded, can also be $C_5$-$C_7$-cycloalkyl which is unsubstituted or bears 1, 2 or 3 substituents mutually independently selected from $C_1$-$C_6$-alkyl and $C_2$-$C_6$-alkenyl; and
b) the reaction product from step a) is optionally treated with an acid.

The invention also provides the compounds of the general formula (I) and (I') obtainable by this process.

The invention further provides a cosmetic or pharmaceutical composition which comprises at least one compound of the general formula (I) or (I') as defined above and below.

The invention further provides the use of compounds of the general formula (I) or (I') as defined above and below as surface-active substances, especially as surfactant for detergents and cleaners, cosmetic compositions or pharmaceutical compositions.

DESCRIPTION

The compounds of the general formula (I) can be used in the form of mixtures or in the form or pure compounds. Materials suitable for the inventive uses are generally mixtures of compounds of the general formula (I) which are obtainable by way of example through the production process described below. The individual components of these mixtures can by way of example differ in respect of the degree of alkoxylation k. The individual components of these mixtures can moreover differ in respect of the degree of oligomerization n. It is, of course, also possible to separate the reaction mixtures obtainable by the process of the invention by using conventional separation methods, e.g. by distillation or by chromatography.

For the purposes of the invention, cation equivalent means one monovalent cation or the monovalent-charged portion of a polyvalent cation. When A or A' is one cation equivalent, this is preferably selected from alkali metal cations, $NH_4^+$ and cations of the formula $HNE^1E^2E^{3+}$, where $E^1$, $E^2$ and $E^3$ are mutually independently selected from hydrogen, linear and branched $C_1$-$C_6$-alkyl and linear and branched $C_1$-$C_4$-hydroxyalkyl, with the proviso that one of the moieties $E^1$, $E^2$ and $E^3$ differs from hydrogen. It is preferable that the cation equivalent is selected from $Na^+$, $K^+$, $NH_4^+$, $Mg^{2+}/2$, $HN(CH_3)_3^+$, $HN(C_2H_5)_3^+$, $HN(C_2H_4OH)_3^+$, $H_2N(C_2H_4OH)_2^+$, etc. In particular, the cation equivalent is one alkali metal cation or one equivalent of an alkaline earth metal cation.

Suitable linear or branched saturated or unsaturated aliphatic hydrocarbon moieties having from 1 to 30 carbon atoms are the corresponding $C_1$-$C_{30}$-alkyl moieties and $C_1$-$C_{30}$-alkenyl moieties having 1, 2, 3 or more than 3 C—C double bonds.

Unsaturated aliphatic hydrocarbon moieties having from 1 to 30 carbon atoms generally have 1, 2 or 3 double bonds.

A specific embodiment involves mainly the linear alkyl moieties that also occur in natural or synthetic fatty alcohols, and also in oxo alcohols, or involves namely the linear alkenyl moieties that also occur in natural or synthetic fatty alcohols, and also oxo alcohols, where these can have single, double, triple, quadruple, pentuple or sixtuple unsaturation.

When one of the moieties R, $R^1$, $R^3$, $R^{1'}$ and $R^{3'}$ is alkyl or alkenyl, these moieties preferably derive from natural raw materials, particularly preferably from a renewable raw material.

Suitable $C_1$-$C_{25}$-alkyl groups, $C_1$-$C_{20}$-alkyl groups and $C_1$-$C_6$-alkyl groups are respectively linear and branched alkyl groups.

Suitable $C_2$-$C_{30}$-alkenyl groups, $C_2$-$C_{25}$-alkenyl groups and $C_2$-$C_6$-alkenyl groups are respectively linear and branched alkenyl groups having respectively 1, 2, 3 or more than 3 C—C double bonds.

Suitable $C_2$-$C_{10}$-alkylene groups, $C_{10}$-$C_{30}$-alkylene groups and $C_{10}$-$C_{20}$-alkylene groups are respectively linear and branched alkylene groups.

For the purposes of the present invention, $C_1$-$C_6$-alkyl is a linear or branched alkyl moiety having from 1 to 6 carbon atoms. Examples here are methyl, ethyl, propyl, isopropyl, n-butyl, sec-butyl, isobutyl, tert-butyl, pentyl, hexyl and positional isomers thereof.

$C_1$-$C_{20}$-Alkyl is the abovementioned $C_1$-$C_6$-alkyl moieties, and also linear or branched alkyl moieties having from 7 to 20 carbon atoms. Examples thereof are n-heptyl, n-octyl, 2-ethylhexyl, n-nonyl, n-decyl, 2-propylheptyl, n-undecyl, n-dodecyl, n-tridecyl, isotridecyl, n-tetradecyl, n-pentadecyl, n-hexadecyl, n-heptadecyl, n-octadecyl (stearyl), isostearyl, n-nonadecyl, n-eicosyl (arachinyl), and positional isomers thereof.

$C_1$-$C_{25}$-Alkyl is the abovementioned $C_1$-$C_{20}$-alkyl moieties, and also a linear or branched alkyl moiety having from 21 to 25 carbon atoms. Examples here are n-henicosyl, n-docosyl (behenyl), n-tricosyl, n-tetracosyl (behenyl), n-pentacosyl and positional isomers thereof.

$C_1$-$C_{30}$-Alkyl is the abovementioned $C_1$-$C_{25}$-alkyl moieties, and also linear or branched alkyl moieties having from 26 to 30 carbon atoms.

For the process of the present invention, $C_2$-$C_6$-alkenyl is linear or branched alkenyl moieties having 1 or 2 C—C double bonds. Examples here are ethenyl, n-propenyl, allyl, n-butenyl, n-butadienyl, n-pentenyl, n-pentadienyl, n-hexenyl, n-hexadienyl and structural isomers of these.

$C_2$-$C_{25}$-Alkenyl is the abovementioned $C_2$-$C_6$-alkenyl moieties, and also a linear or branched alkenyl moiety having from 7 to 25 carbon atoms and having 1, 2, 3 or more than 3 C—C double bonds. Examples here are n-heptenyl, n-octenyl, n-octadienyl, n-octatrienyl, n-nonenyl, n-nonadienyl, n-nonatrienyl, n-decenyl, n-decadienyl, n-decatrienyl, n-dodecenyl, n-dodecadienyl, n-dodecatrienyl, n-tridecenyl, n-tridecadienyl, n-tridecatrienyl, n-tetradecenyl, n-tetradecadienyl, n-tetradecatrienyl, n-hexadecenyl, n-hexadecadienyl, n-hexadecatrienyl, n-heptadecenyl, n-heptadecadienyl, n-heptadecatrienyl, n-octadecenyl, n-octadecadienyl, n-octadecatrienyl, n-nonadecenyl, n-nonadecadienyl, n-nonadecatrienyl, n-eicosenyl, n-eicosadienyl, n-eicosatrienyl, n-heneicosenyl, n-heneicosadienyl, n-heneicosatrienyl, n-docosenyl, n-docosadienyl, n-docosatrienyl, n-tricosenyl, n-tricosadienyl, n-tricosatrienyl, n-tetracosenyl, n-tetracosadienyl, n-tetracosatrienyl, oleyl, linolenyl and structural isomers of these.

$C_2$-$C_{30}$-Alkenyl is the abovementioned $C_2$-$C_{25}$-alkenyl moieties, and also a linear or branched alkenyl moiety having from 26 to 30 carbon atoms and having 1, 2, 3 or more than 3 C—C double bonds.

$C_2$-$C_{10}$-Alkylene is preferably linear or branched and is preferably selected from —$CH_2CH_2$—, —$CH(CH_3)$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH(CH_3)$—$C_5H_{10}$—, —$C_6H_{12}$—, —$C_7H_{14}$—, —$C_8H_{16}$—, —$C_9H_{18}$—, —$C_{10}H_{20}$— and structural isomers of these.

For the process of the present invention, a saturated or unsaturated cycloaliphatic hydrocarbon moiety having from 3 to 10 carbon atoms is cycloalkanyl or cycloalkenyl, where the ring has from 3 to 10 carbon atoms. These cycloaliphatic hydrocarbon moieties can respectively be unsubstituted or substituted. Saturated unsubstituted cycloaliphatic hydrocarbon moieties are preferably cyclopropyl, cyclobutyl, cyclopentyl, cyclohexyl, cycloheptyl and cyclooctyl. Saturated substituted cycloaliphatic hydrocarbon moieties preferably bear 1, 2 or 3 substituents mutually independently selected from $C_1$-$C_6$-alkyl and $C_2$-$C_6$-alkenyl. Unsaturated unsubstituted cycloaliphatic hydrocarbon moieties are preferably cyclopropenyl, cyclobutenyl, cyclopentenyl, cyclohexenyl, cycloheptenyl and cyclooctenyl. Unsaturated substituted cycloaliphatic hydrocarbon moieties preferably bear 1, 2 or 3 substituents mutually independently selected from $C_1$-$C_6$-alkyl and $C_2$-$C_6$-alkenyl.

For the purposes of the present invention, $C_5$-$C_7$-cycloalkyl is a monocyclic saturated or unsaturated hydrocarbon ring having from 5 to 7 carbon atoms. Examples of unsubstituted $C_5$-$C_7$-cycloalkyl are cyclopentyl, cyclohexyl and cycloheptyl. Examples of substituted $C_5$-$C_7$-cycloalkyl are methylcyclopentyl, ethylcyclopentyl, n-propylcyclopentyl, isopropylcyclopentyl, methylcyclohexyl, ethylcyclohexyl, n-propylcyclohexyl, isopropylcyclohexyl, isopropenylcyclohexyl and isobutenylcyclopropyl.

For the purposes of the present invention, a divalent saturated or unsaturated cycloaliphatic hydrocarbon moiety having from 3 to 10 carbon atoms is cycloalkanediyl or cycloalkenediyl, where the ring has from 3 to 10 carbon atoms. Examples of divalent saturated cycloaliphatic hydrocarbon moieties are cyclopropane-1,2-diyl, cyclobutane-1,3-diyl, cyclopentane-1,2-diyl, cyclohexane-1,4-diyl and cycloheptane-1,3-diyl.

For the purposes of the present invention, aryl is a carbocyclic aromatic radical having from 6 to 14 carbon atoms. Examples here are phenyl, naphthyl, fluorenzyl, azulenyl, anthracenyl and phenanthrenyl. Aryl is preferably phenyl or naphthyl, in particular phenyl. The aryl moieties can respectively be unsubstituted or substituted. Substituted aryl moieties preferably bear 1, 2 or 3 substituents mutually independently selected from $C_1$-$C_6$-alkyl and $C_2$-$C_6$-alkenyl. Among these are by way of example tolyl, xylylenyl, ethylphenyl, n-propylphenyl, isopropylphenyl, isopropenylphenyl and isobutenylphenyl.

A preferred embodiment of the invention is provided by compounds of the formula (I')

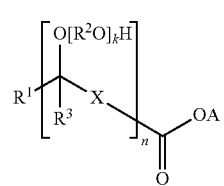

(I')

in which $R^1$ is selected from hydrogen, a linear or branched saturated or unsaturated aliphatic hydrocarbon moiety having from 1 to 30 carbon atoms, saturated or unsaturated cycloaliphatic hydrocarbon moieties having from 3 to 10 carbon atoms and aryl, $R^3$ is selected from hydrogen and methyl, X is respectively a bond or a divalent linear or branched saturated or unsaturated aliphatic hydrocarbon moiety having from 1 to 30 carbon atoms, or a divalent saturated or unsaturated cycloaliphatic hydrocarbon moiety from 3 to 10 carbon atoms;

n is a number from 1 to 10; and

A is a hydrogen or one cation equivalent;

k is a number from 1 to 100; and $R^2$ is a divalent linear or branched saturated aliphatic hydrocarbon moiety having from 2 to 30 carbon atoms.

It is preferable that $R^2$ is —$CR^aR^b$—$CR^cR^d$—, in which each $R^a$, $R^b$, $R^c$ and $R^d$ is mutually independently selected from hydrogen, $C_1$-$C_{20}$-alkyl, unsubstituted $C_5$-$C_7$-cycloalkyl and $C_5$-$C_7$-cycloalkyl having 1, 2 or 3 $C_1$-$C_6$-alkyl substituents. In particular, each $R^a$ is independently hydrogen, $C_1$-$C_{20}$-alkyl or unsubstituted $C_5$-$C_7$-cycloalkyl.

It is preferable that $R^b$ is independently hydrogen or $C_1$-$C_6$-alkyl, in particular hydrogen or methyl, especially hydrogen.

It is preferable that each $R^c$ is independently hydrogen or $C_1$-$C_6$-alkyl, in particular hydrogen or methyl, especially hydrogen.

It is preferable that each $R^d$ is independently hydrogen or $C_1$-$C_6$-alkyl, in particular hydrogen or methyl.

In a preferred embodiment, $R^2$ is —$CR^aR^b$—$CR^cR^d$—, in which each $R^a$ is mutually independently selected from hydrogen, $C_1$-$C_{20}$-alkyl, unsubstituted $C_5$-$C_7$-cycloalkyl, $C_5$-$C_7$-cycloalkyl having 1, 2 or 3 $C_1$-$C_6$-alkyl substituents, each $R^b$ and $R^d$ is hydrogen and each $R^c$ is hydrogen or methyl.

When the moiety $R^2$ in the $-O-[R^2-O]_k-H$ groups is $-CR^aR^b-CR^cR^d-$, in which $CR^aR^b$ and $CR^cR^d$ are not identical (i.e. the two carbon atoms are differently substituted), the orientation of each $-CR^aR^b-CR^cR^d-$ moiety is in principle as desired. In other words, each moiety $R^2$ can be $-CR^aR^b-CR^cR^d-$ or $-CR^cR^d-CR^aR^b-$. All of the moieties $R^2$ of an alkoxylate chain generally have the same orientation. The conditions of the alkoxylation reaction, and especially the catalyst used, determine whether the more highly substituted carbon atom is closer to, or further from, the hydroxycarboxylic-acid-bearing end of the alkoxylate chain. Without any intention of adopting any particular theory, under acidic conditions the reaction during nucleophilic ring-opening generally proceeds by an $S_N1$ mechanism, i.e. the oxygen atom of the hydroxycarboxylic acid or the terminal oxygen atom of the growing chain end bonds to the more highly substituted carbon atom of the $-CR^aR^b-CR^cR^d-$ moieties, because the stabiler, i.e. the more highly substituted, carbocation is formed as intermediate.

To the extent that the variable n in the groups of the formula $-(R^2-O)_n-R^3$ is at least 2, the moieties $R^2$ of the individual repeater units can be identical or different. The sequence of the alkylene oxide units ($R^2-O$) is in principle as desired.

k is particularly a number from 1 to 50, in particular from 1 to 20, especially from 1 to 10.

A is preferably hydrogen or an alkali metal cation or one equivalent of an alkaline earth metal cation, in particular hydrogen, $K^+$, $Na^+$ or $\frac{1}{2}Mg^{2+}$.

$R^1$ is particularly selected from hydrogen, $C_1$-$C_{25}$-alkyl, $C_1$-$C_{25}$-alkenyl, and phenyl.

$R^1$ is particularly preferably selected from hydrogen, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, etc., in particular methyl, ethyl, n-propyl, isopropyl, n-butyl, isobutyl, sec-butyl, tert-butyl, n-pentyl, isoamyl, n-hexyl, 2-ethylhexyl, n-heptyl, n-octyl, n-nonyl, n-decyl, 2-propylheptyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl or linolenyl.

$R^1$ is in particular selected from hydrogen and $C_1$-$C_{10}$-alkyl.

X is preferably a bond, $C_1$-$C_{20}$-alkylene, or $C_2$-$C_{20}$-alkenylene, in particular a bond, $C_1$-$C_{15}$-alkylene or $C_2$-$C_{15}$-alkenylene, especially a bond, $C_1$-$C_{12}$-alkylene or $C_2$-$C_{12}$-alkenylene.

$R^3$ is preferably hydrogen.

n is preferably 1 or 2, in particular 1.

The saponification value of the compounds of the formula (I) of the invention is smaller than 10 mg KOH/g, preferably smaller than 9 mg KOH/g, particularly smaller than 8 mg KOH/g.

The invention further provides a process for the production of compounds of the general formula (I), where a) at least one hydroxycarboxylic salt of the general formula (III)

$$R'-C(=O)-O-A' \quad (III)$$

in which

R' is an organic moiety which bears at least one hydroxy group and in which all of the optionally comprised acid groups have been fully deprotonated; and each A' is respectively independently one cation equivalent;

is reacted with at least one epoxide of the general formula (IV)

in which each $R^a$, $R^b$, $R^c$ and $R^d$ is mutually independently selected from hydrogen, unsubstituted $C_1$-$C_{30}$-alkyl and unsubstituted $C_5$-$C_7$-cycloalkyl and $C_5$-$C_7$-cycloalkyl which bears 1, 2 or 3 substituents which are mutually independently selected from $C_1$-$C_6$-alkyl and $C_2$-$C_6$-alkenyl, where two moieties $R^a$ and $R^c$, together with the $-CR^b-CR^d-$ group to which they are bonded, can also be $C_5$-$C_7$-cycloalkyl which is unsubstituted or bears 1, 2 or 3 substituents mutually independently selected from $C_1$-$C_6$-alkyl and $C_2$-$C_6$-alkenyl; and b) the reaction product from step a) is optionally treated with an acid.

Step a)

The alkoxylation reaction in step a) can take place in a plurality of stages where at least one hydroxycarboxylic salt (III) is first reacted with an epoxide of the general formula (IV) and then, optionally after separation and/or purification, the resultant reaction mixture is reacted with at least one further epoxide of the general formula (IV) in a subsequent alkoxylation reaction.

The alkoxylation reaction for the production of compounds of the general formula (I) is preferably a one-pot reaction in which at least one hydroxycarboxylic salt of the general formula (III) is subjected to alkoxylation in the presence of at least one epoxide of the general formula (IV).

The compounds of the formula (III) can optionally comprise acid groups. The acid groups comprised are present in fully deprotonated form.

The compound (I) is obtained via a reaction of a hydroxycarboxylic salt of the general formula (III) or (III') with an epoxide of the general formula (IV). The reaction conditions for the reaction of the alcohol with an alkylene oxide can be selected by methods known to the person skilled in the art.

The alkoxylation can take place randomly, in alternating manner or blockwise. Step a) of the process of the invention provides a compound $R'-C(=O)-O-A'$ (III).

Preferred compounds (III) for the use in step a) are hydroxycarboxylic salts where a salt of the formula (III') is used as hydroxycarboxylic salt

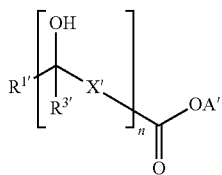

(III')

in which
R¹' is defined as stated above for R¹;
R³' is defined as stated above for R³;
X' is a defined as stated above for X;
n is defined as stated above; and
A' is one cation equivalent.

In respect of suitable and preferred definitions of R¹', R³', X', A' and n, reference is made to the entirety of what has been said above in relation to these moieties and variables.

In a preferred embodiment, the hydroxycarboxylic salt is selected from salts of lactic acid, glycolic acid, 12-hydroxystearic acid, ricinoleic acid, 3-hydroxybutytic acid, 4-hydroxybutytic acid, mandelic acid and mixtures thereof.

In a particularly preferred embodiment, the hydroxycarboxylic salt is selected from salts of lactic acid, 12-hydroxystearic acid and ricinoleic acid.

In a preferred embodiment, the alkylene oxide is selected from ethylene oxide, propylene oxide, 1,2-butylene oxide, 2,3-butylene oxide, $C_{10}$-$C_{30}$-alkylene oxides and mixtures thereof. In particular, the alkylene oxide is selected from ethylene oxide, propylene oxide, 1,2-butylene oxide, 2,3-butylene oxide, hexadecene epoxide and dodecene epoxide.

The quantity of epoxide (IV) used per mole of the compound (III) is generally from 1 to 8 mol, preferably from 2 to 7 mol. Any remaining unreacted epoxide (IV) can be removed by distillation or by stripping with an inert gas, for example nitrogen or argon.

The first stage of the step a) generally uses from 1 to 7 mol, preferably from 2 to 6 mol, of the epoxide (IV) per mole of the compound (III). The second stage of the step a) generally uses from 0.5 to 2 mol, preferably from 1 to 1.5 mol, of the epoxide (IV) per mole of the compound (III).

The temperature at which the reaction in step a) takes place is usually from 50° C. to 180° C., preferably from 85° C. to 160° C., particularly preferably from 95° C. to 150° C.

The alkoxylation preferably takes place at atmospheric pressure or reduced pressure. If the alkoxylation is carried out at reduced pressure, the pressure is preferably in the range from 1 mbar to 1.1 bar, in particular from 5 mbar to 1 bar, especially from 10 mbar to 900 mbar. This applies to both the single-stage and the two-stage variant of the alkoxylation reaction. It is preferable that the reaction takes place at atmospheric pressure.

The compound (III) from step a) can be heated together with the epoxide (IV) until the desired reaction temperature has been achieved. In another possible method, the compound (III) is first heated to the desired reaction temperature. The epoxide (IV) is added thereto at the desired reaction temperature.

It is preferable that the compound (III) is heated to the reaction temperature. The epoxide (IV) is added thereto at reaction temperature. This can take place in one or more steps at various temperatures. The addition can also take place over a prolonged period, during which the temperature can be kept constant or continuously increased. Once addition of the epoxide (IV) is complete, the mixture can be kept for a certain time at the reaction temperature or at another temperature.

It is preferable that the epoxide (IV) is added in a plurality of steps. It is preferable here that two different epoxides (IV) are added in the different steps. The first stage in step a) reacts the salt of the hydroxycarboxylic acid (III) with at least one first epoxide (IV). The first epoxide (IV) for the reaction in step a) in the first stage is preferably selected from ethylene oxide, propylene oxide, butylene 1,2-oxide and butylene 2,3-oxide. The product obtained from the first stage is reacted in a second stage with a second epoxide (IV). The second epoxide (IV) is preferably selected from $C_{10}$-$C_{20}$-epoxides (IV), in particular selected from hexadecene epoxide and dodecene epoxide.

The alkoxylation can take place autocatalytically or in the presence of a catalyst.

Compounds generally used as catalyst are alkali metals, hydroxides of alkali metals or of alkaline earth metals, alcoholates of alkali metals or of alkaline earth metals, acetates of alkali metals or of alkaline earth metals, hydrides of alkali metals or of alkaline earth metals, phosphanes, double-metal cyanides, Lewis acids or tertiary amines.

Preferred alkali metals are lithium, sodium and potassium, particularly potassium.

Preferred hydroxides of alkali metals or of alkaline earth metals are lithium hydroxide, sodium hydroxide, potassium hydroxide, calcium hydroxide and barium hydroxide, particularly lithium hydroxide, sodium hydroxide and potassium hydroxide.

Preferred alcoholates of alkali metals or of alkaline earth metals are sodium methanolate, potassium methanolate, sodium ethanolate, potassium ethanolate and potassium tert-butanolate, particularly sodium methanolate and potassium methanolate.

Preferred acetates of alkali metals or of alkaline earth metals are sodium acetate (NaOAc) and potassium acetate (KOAc), particularly sodium acetate (NaOAc).

Preferred hydrides of alkali metals or of alkaline earth metals are lithium hydride, sodium hydride and potassium hydride, particularly sodium hydride.

Preferred phosphane is triphenylphosphane.

Preferred Lewis acids are $B(CH_3)_3$, $B(OH)_3$, $BF_3$, $B(Cl)_3$, $AlCl_3$, $Al(OEt)_3$ and $Ti(OiPr)_4$, particularly $BF_3$.

Preferred tertiary amines are trimethylamine, triethylamine, tris(ethylhexylamine), tripropylamine, tributylamine, trihexylamine, trioctylamine and pyridine.

Preferred double-metal cyanides are $Mn_3[Co(CN)_6]_2$ and $Zn_3[Co(CN)_6]_2$.

The quantity used of the catalyst is preferably from 0.01 to 5 mol %, based on the hydroxycarboxylic salt (III).

The alkylation reaction preferably takes place in the absence of a catalyst.

The reaction in step a) can be carried out in the presence of a solvent that is inert under the reaction conditions. Examples of these solvents are tetrahydrofuran, methyl tert-butyl ether, dioxane, toluene and xylene. It is also possible to carry out the reaction in bulk, i.e. without external (added) solvents.

The reaction of the invention can be carried out continuously or batchwise, preferably batchwise.

The reaction of the invention can be carried out in a stored tank, a reactor with pump circulation, a stirred-tank cascade or a tubular reactor, preferably a stirred tank or reactor with pump circulation.

Step b)

Step b) is optional. It can optionally be advantageous to treat the reaction product from step a) with an acid in order to obtain the alkoxylated hydroxycarboxylic acid.

Compounds used for this purpose are generally carboxylic acids, sulfonic acids, $CO_2$ or mineral acids. It is also possible to use ion exchangers. Preference is given to carboxylic acids and mineral acids, particularly carboxylic acids.

A preferred carboxylic acid is acetic acid. Particular preference is given to glacial acidic acid.

The invention further provides alkoxylated hydroxycarboxylic acids or salts of these of the formula (I) or (I') and mixtures thereof, these being obtainable by the process described above.

The compounds of the general formula (I) and of the general formula (I') are advantageously suitable for use as surfactants. Materials involved here can very generally by way of example be cosmetic compositions, pharmaceutical compositions, hygiene products, detergents, paints, compositions for the paper industry, compositions for the textile industry, etc.

The surfactants of the invention can be used here as sole surface-active substance. The compounds of the general formula (I) and of the general formula (I') advantageously feature good compatibility with other surfactants.

Surfactant-Containing Compositions

The compounds of the general formula (I) or of the general formula (I') of the invention have particularly advantageous suitability for the formulation of surfactant-containing compositions. These are in particular aqueous surfactant-containing compositions. The compounds (I) or (I') in compositions of this type feature good water-solubility, good compatibility with many of the active ingredients and auxiliaries used in cosmetics, good foaming properties and good rheology.

The total surfactant content of the surfactant-containing compositions of the invention is, based on the total weight of the surfactant-containing composition, preferably from 0.1 to 75% by weight, particularly preferably from 0.5 to 60% by weight, in particular from 1 to 50% by weight.

Suitable surfactants, where these differ from the compounds (I) and (I'), are anionic surfactants, nonionic surfactants, cationic surfactants, amphoteric surfactants and mixtures thereof.

Typical examples of anionic surfactants are soaps, alkylsulfonates, alkylbenzenesulfonates, olefinsulfonates, alkyl ether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, for example acyl glutamates and acyl aspartates, and also acyl lactylates, acyl tartrates, alkyl oligoglucoside sulfates, alkyl glucose carboxylates, protein fatty acid condensates and alkyl (ether) phosphates.

Examples of suitable soaps are the alkali metal, alkaline earth metal and ammonium salts of fatty acids, for example potassium stearate.

Suitable olefinsulfonates are obtained by way of example by an addition reaction between $SO_3$ and olefins of the formula $R^5$—CH=CH—$R^4$ and subsequent hydrolysis and neutralization, where $R^5$ and $R^4$ are mutually independently H or alkyl moieties having from 1 to 20 carbon atoms, with the proviso that $R^5$ and $R^4$ together have at least 6 carbon atoms and preferably from 8 to 20 carbon atoms, especially from 10 to 16 carbon atoms. In respect of production and use, reference may be made to review article "J. Am. Oil. Chem. Soc.", 55, 70 (1978). The olefinsulfonates can take the form of alkali metal salts, alkaline earth metal salts, ammonium salts, alkylammonium salts, alkanolammonium salts or glucammonium salts. The olefinsulfonates preferably take the form of sodium salts. The hydrolyzed alpha-olefin sulfonation products, i.e. the alpha-olefinsulfonates, are composed of a combination of about 60% by weight of alkanesulfonates and about 40% by weight of hydroxyalkanesulfonates; about 80 to 85% by weight of these are monosulfonates, and about 15 to 20% by weight of these are disulfonates.

Preferred methyl ester sulfonates (MES) are obtained via sulfonation of the fatty acid methyl esters of vegetal or animal fats or oils. Preference is given to methyl ester sulfonates derived from vegetable fats and oils, e.g. from rapeseed oil, sunflower oil, soy oil, palm oil, coconut fat, etc.

Preferred alkyl sulfates are sulfates of fatty alcohols of the general formula $R^6$—O—$SO_3Y$, in which $R^6$ is a linear or branched, saturated or unsaturated hydrocarbon moiety having from 6 to 22 carbon atoms and Y is an alkali metal, the monovalent-charged equivalent on an alkaline earth metal, or is ammonium or mono-, di-, tri- or tetraalkylammonium, alkanolammonium or glucammonium. Suitable fatty alcohol sulfates are preferably obtained via sulfation of native fatty alcohols or of synthetic oxo alcohols and subsequent neutralization. Typical examples of fatty alcohol sulfates are the sulfation products of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, behenyl alcohol and elaeostearyl alcohol, other examples being the salts and mixtures thereof. Preferred salts of the fatty alcohol sulfates are the sodium salts and potassium salts, in particular the sodium salts. Preferred mixtures of the fatty alcohol sulfates are based on technical alcohol mixtures which by way of example arise during the high-pressure hydrogenation of technical methyl esters based on fats and on oils, or during the hydrogenation of aldehydes derived from the oxo synthesis, or during the dimerization of unsaturated fatty alcohols. Compounds preferably used for the production of alkyl sulfates are fatty alcohols and fatty alcohol mixtures having from 12 to 18 carbon atoms and in particular from 12 to 14 carbon atoms. Typical examples of these are technical alcohol sulfates based on vegetable feedstocks.

Preferred sarcosinates are sodium lauroyl sarcosinate and sodium stearoyl sarcosinate.

Preferred protein fatty acid condensates are vegetable products based on wheat.

Preferred alkyl phosphates are mono- and diphosphoric alkyl esters.

Suitable acyl glutamates are compounds of the formula (V)

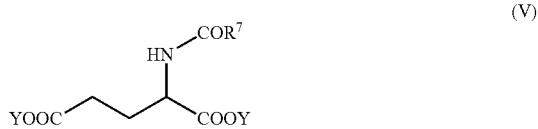

in which COR⁷ is a linear or branched acyl moiety having from 6 to 22 carbon atoms and 0, 1, 2 or 3 double bonds, and Y is hydrogen, an alkali metal, the monovalent-charged equivalent of an alkaline earth metal, or is an ammonium, alkylammonium, alkanolammonium or glucammonium. Acyl glutamates are produced by way of example via Schotten-Baumann acylation of glutamic acid with fatty acids, fatty acid esters or fatty acid halides. Acylglutamates are obtainable commercially by way of example from BASF SE, Clariant AG, Frankfurt/DE, or Ajinomoto Co. Inc., Tokyo/JP. A review of production and properties of acyl glutamates by M. Takehara et al. is found in J. Am. Oil Chem. Soc. 49 (1972) 143. Typical suitable acyl glutamates preferably derive from fatty acids having from 6 to 22 carbon atoms, particularly preferably from 12 to 18 carbon atoms. In particular, the mono- or dialkali-metal salts of the acyl glutamate are used. Among these are by way of example (trademarks of Ajinomoto, USA in brackets): sodium cocoyl glutamate (Amisoft CS-11), disodium cocoyl glutamate (Amisoft ECS-22SB), triethanolammonium cocoyl glutamate (Amisoft CT-12), triethanolammonium lauroyl glutamate (Amisoft LT-12), sodium myristoyl glutamate (Amisoft MS-11), sodium stearoyl glutamate (Amisoft HS-11 P) and mixtures thereof.

Among the nonionic surfactants are by way of example:
fatty alcohol polyoxyalkylene esters, for example lauryl alcohol polyoxymethylene acetate,
alkyl polyoxyalkylene ethers which derive from low-molecular-weight $C_1$-$C_6$-alcohols or from $C_7$-$C_{30}$-fatty alcohols. The ether component here can derive from ethylene oxide units, propylene oxide units, butylene 1,2-oxide units, butylene 1,4-oxide units or from random copolymers or block copolymers thereof. Among these are especially fatty alcohol alkoxylates and oxo alcohol alkoxylates, in particular of the RO—$(R^8O)_r$—$(R^9O)_sR^{10}$ type, where $R^8$ and $R^9$ mutually independently=$C_2H_4$, $C_3H_6$, $C_4H_8$ and $R^{10}$=H or $C_1$-$C_{12}$-alkyl, R=$C_3$-$C_{30}$-alkyl or $C_6$-$C_{30}$-alkenyl, r and s being mutually independently from 0 to 50, but not both 0, for example isotridecyl alcohol polyoxyethylene ether and oleyl alcohol polyoxyethylene ether,
alkylaryl alcohol polyoxyethylene ethers, e.g. octylphenol polyoxyethylene ether,
alkoxylated animal and/or vegetable fats and/or oils, for example corn oil ethoxylates, castor oil ethoxylates, tallow fatty ethoxylates,
glycerol esters, for example glycerol monostearate,
alkylphenol alkoxylates, for example ethoxylated isooctyl-, octyl- or nonylphenol or tributylphenol polyoxyethylene ether,
fatty amine alkoxylates, fatty acid amide alkoxylates and fatty acid diethanolamide alkoxylates, and in particular ethoxylates of these,
sugar surfactants, sorbitol esters, for example sorbitan fatty acid esters (sorbitan monooleate, sorbitan tristearate), polyoxyethylene sorbitan fatty acid esters, alkyl polyglycosides, N-alkylgluconamides,
alkyl methyl sulfoxides,
alkyldimethylphosphine oxides, for example tetradecyldimethylphosphine oxide.

Examples of suitable amphoteric surfactants are alkylbetaines, alkylamidopropylbetaines, alkylsulfobetaines, alkyl glycinates, alkylcarboxyglycinates, alkylamphoacetates and -propionates, alkylamphodiacetates and -dipropionates. By way of example, it is possible to use cocodimethylsulfopropylbetaine, laurylbetaine, cocamidopropylbetaine, sodium cocamphopropionate or tetradecyldimethylamine oxide.

Among the cationic surfactants are by way of example quaternized ammonium compounds, in particular alkyltrimethylammonium halides and dialkyldimethylammonium halides and the corresponding alkyl sulfates, and also pyridine derivatives and imidazoline derivatives, in particular alkylpyridinium halides. By way of example, it is possible to use behenyl or cetyltrimethylammonium chloride. Other compounds that are moreover suitable are those known as ester quats, which are based on quaternary triethanolmethylammonium compounds or quaternary diethanoldimethylammonium compounds having long hydrocarbon chains in the form of fatty acid esters. Among these are by way of example bis(acyloxyethyl)hydroxyethylammonium methosulfate. Another suitable material is Dehyquart L 80 (INCI: dicocoylethyl hydroxyethylammonium methosulfate (and) propylene glycol).

Cosmetic and Pharmaceutical Compositions

The compounds of the general formula (I) and of the general formula (I') are preferably suitable for the formulation of cosmetic and pharmaceutical products, especially of aqueous cosmetic and pharmaceutical products.

The invention further provides a cosmetic or pharmaceutical composition comprising
a) at least one compound of the general formula (I) or (I'), as defined above,
b) at least one cosmetic or pharmaceutical active ingredient, and
c) optionally at least one cosmetic or pharmaceutical auxiliary different from components a) and b).

It is preferable to use, as component a), at least one compound of the general formula (I).

It is preferable that component c) comprises at least one cosmetic or pharmaceutical carrier.

It is preferable that the carrier component c) is selected from
i) water,
ii) water-miscible organic solvents, preferably $C_2$-$C_4$-alkanols, in particular ethanol,
iii) oils, fats and waxes,
iv) esters of $C_6$-$C_{30}$-monocarboxylic acids with mono-, di- or trihydric alcohols, where said esters differ from iii),
v) saturated acyclic and cyclic hydrocarbons,
vi) fatty acids,
vii) fatty alcohols,
viii) propellant gases,
and mixtures thereof.

Oil components or fat components c) that are compatible in cosmetics and are especially suitable are described in Karl-Heinz Schrader, Grundlagen und Rezepturen der Kosmetika [Principles and formulations of cosmetics], 2nd edn., Verlag Hüthig, Heidelberg, pp. 319-355, which is hereby incorporated by way of reference.

The cosmetic compositions of the invention can be skin-cosmetic, hair-cosmetic, dermatological, or pharmaceutical compositions or compositions for hygiene purposes. Because the compounds described above of the formula (I) and of the formula (I') have properties relating to activity at interfaces, they are in particular suitable in compositions for cleaning of the skin and/or of the hair.

It is preferable that the compositions of the invention take the form of an aqueous solution, of a solid formulation (e.g. of a bar of soap or of a wash stick), of a foam, or of an emulsion, suspension, lotion, gel, paste or spray. It is also possible, if desired, to use liposomes or microspheres.

The cosmetic compositions of the invention can also comprise cosmetic and/or dermatological active ingredients and substances providing special cosmetic and/or dermatological effects, and also auxiliaries. It is preferable that the cosmetic compositions of the invention comprise at least one compound of the formula (I) or of the formula (I'), as defined above, at least one carrier as defined above, C), and at least one constituent that differs therefrom, preferably selected from cosmetic active ingredients, emulsifiers, surfactants, preservatives, fragrances, additional thickeners, hair polymers, hair conditioners and skin conditioners, graft polymers, water-soluble or dispersible silicone-containing polymers, light stabilizers, bleaching agents, gel-formers, skincare agents, tinting agents, tanning agents, dyes, pigments, consistency regulators, humectants, refatting agents, collagen, protein hydrolysates, lipids, antioxidants, antifoams, antistatic agents, emollients and softeners.

The cosmetic compositions can comprise, in addition to the compounds of the formula (I) and the formula (I'), at least on thickener. Among these are by way of example polysaccharides and organic sheet minerals such as Xanthan Gum® (Kelzan® from Kelco), Rhodopol® 23 (Rhone Poulenc) or Veegum® (R. T. Vanderbilt) or Attaclay® (Engelhardt). Other suitable thickeners are natural organic thickeners (Agar, Carrageen, Tragant, gum arabic, alginates, pectins, polyoses, guar flour, carob seed flour, starch, dextrins, gelatins, casein) and inorganic thickeners (polysilicas, clay minerals such as montmorillonites, zeolites, silicas). Other thickeners are polysaccharide gums, for example gum arabic, agar, alginates, carrageens and their salts, guar, guaran, tragacanth, gellan, ramsan, dextran and xanthan and their derivatives, e.g. propoxylated guar, and also their mixtures. Examples of other polysaccharide thickeners are starch from a very wide variety of sources and starch derivatives, e.g. hydroxyethyl starch, starch phosphate esters and starch acetates and carboxymethylcellulose and the sodium salt thereof, methyl-, ethyl-, hydroxyethyl-, hydroxypropyl-, hydroxypropylmethyl- and hydroxyethylmethylcellulose and cellulose acetate. Phyllosilicates can moreover be used as thickeners. Among these are by way of example the magnesium or sodium magnesium phyllosilicates obtainable with trademark Laponite® from Solvay Alkali, and also the magnesium silicates from Süd-Chemie.

Examples of suitable cosmetic and/or dermatological active ingredients are skin- and hair-pigmented agents, tanning agents, bleaching agents, keratin-hardening substances, antimicrobial active ingredients, light-filtering active ingredients, repellent active ingredients, hyperemic substances, keratolytic and keratoplastic substances, antidandruff active ingredients, antiphlogistic agents, keratinizing substances, active ingredients which are antioxidative or which act as free-radical scavengers, skin-moisturizing or -humectant substances, refatting active ingredients, deodorizing active ingredients, sebostatic active ingredients, plant extracts, antierythimatos or antiallergic active ingredients and mixtures thereof.

Examples of active ingredients which have artificial skin-tanning action and which are suitable for tanning the skin in the absence of natural or artificial UV-irradiation are dihydroxyacetone, alloxan and walnut shell extract. Suitable keratin-hardening substances are generally the active ingredients also used in antitranspirants, i.e. potassium aluminum sulfate, aluminum hydroxychloride, aluminum lactate, etc. Antimicrobial active ingredients are used in order to destroy microorganisms or to inhibit growth thereof, and therefore serve not only as preservatives but also as deodorizing active ingredient which prevents the production of body odor or reduces the intensity thereof. Among these are by way of example conventional preservatives known to the person skilled in the art, for example p-hydroxybenzoic esters, imidazolidinylurea, formaldehyde, sorbic acid, benzoic acid, salicylic acid, etc. Examples of these substances of deodorizing effect are zinc ricinoleate, triclosan, undecylenic acid alkylolamides, citric triethyl ester, chlorhexidine, etc. Suitable light-filter active ingredients are substances which absorb UV radiation in the UV-B and/or UV-A range. Suitable UV filters are the abovementioned. Other suitable materials are p-aminobenzoic esters, cinnamic esters, benzophenones, camphor derivatives, and also pigments providing protection from UV radiation, examples being titanium dioxide, talc powder and zinc oxide. Suitable repellant active ingredients are compounds which are capable of protecting humans from, or of repelling, certain animals, in particular insects. Among these are by way of example 2-ethyl-1,3-hexanediol, N,N-diethyl-m-toluamide, etc. Examples of suitable hyperemic substances which promote flow of blood through the skin are essential oils, for example dwarf pine, lavender, rosemary, juniper, horse chestnut extract, birch leaf extract, hayflower extract, ethyl acetate, camphor, menthol, peppermint oil, rosemary extract, eucalyptus oil, etc. Examples of suitable keratolytic and keratoplastic substances are salicylic acid, calcium thioglycolate, thioglycolic acid and its salts, sulfur, etc. Examples of suitable antidandruff active ingredients are sulfur, sulfur polyethylene glycol sorbitan monooleate, sulfur ricinol polyethoxylate, zinc pyrithione, aluminum pyrithione, etc. Examples of suitable antiphlogistic agents which counteract skin irritations are allantoin, bisabolol, dragosantol, chamomile extract, panthenol, etc.

The cosmetic compositions of the invention can comprise at least one cosmetic or pharmaceutical polymer as cosmetic active ingredient (and also optionally as auxiliary). Among these polymers are very generally anionic, cationic, amphoteric and neutral polymers.

Examples of anionic polymers are copolymers of acrylic acid and acrylamide and salts of these; sodium salts of polyhydroxycarboxylic acids, water-soluble or water-dispersible polyesters, polyurethanes, e.g. Luviset PUR® from BASF, and polyureas. Particularly suitable polymers are copolymers of tert-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally other vinyl esters (e.g. Luviset® grades), maleic anhydride copolymers, optionally reacted with alcohol, anionic polysiloxanes, e.g. those that are carboxy-functional, tert-butyl acrylate, methacrylic acid (e.g. Luviskol® VBM), copolymers of acrylic acid and methacrylic acid with hydrophobic monomers, for example $C_4$-$C_{30}$-alkyl esters of (meth)acrylic acid, $C_4$-$C_{30}$-alkyl vinyl esters, $C_4$-$C_{30}$-alkyl vinyl ethers and hyaluronic acid. Another example of an anionic polymer is the methyl methacrylate/methacrylic acid/acrylic acid/urethane acrylate copolymer obtainable as Luviset® Shape (INCI Name: Polyacrylate-22). Other examples of anionic polymers are the vinyl acetate/crotonic acid copolymers commercially obtainable by way of example as Resyn® (National Starch) and Gafset® (GAF), and vinylpyrrolidone/vinyl acrylate copolymers obtainable by way of example as Luviflex® (BASF). Other suitable polymers are the vinylpyrrolidone/acrylate terpolymer obtainable as Luviflex® VBM-35 (BASF), and sodium-sulfonate-containing polyamides and sodium sulfonate-containing polyesters. Other suitable materials are the vinylpyrrolidone/ethyl methacrylate/methacrylic acid copolymers obtainable from Stepan as Stepanhold-Extra and —R1 and the Carboset® grades from BF Goodrich.

Examples of suitable cationic polymers are cationic polymers with the INCI name polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamidocopolymers (polyquaternium-7) and chitosan. Other suitable cationic (quaternized) polymers are Merquat® (polymer based on dimethyldiallylammonium chloride), Gafquat® (quaternary polymers produced via reaction of polyvinylpyrrolidone with quaternary ammonium compounds), Polymer JR (hydroxyethylcellulose having cationic groups) and vegetable-based cationic polymers, e.g. guar polymers, for example the Jaguar® grades from Rhodia.

Very particularly suitable polymers are neutral polymers, for example polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts of these, polyvinylamines and salts of these, cellulose derivatives, polyaspartic salts and derivatives. Among these are by way of example Luviflex® Swing (partially hydrolyzed copolymer of polyvinyl acetate and polyethylene glycol, BASF).

Other suitable polymers are nonionic, water-soluble or water-dispersible polymers or oligomers, for example polyvinylcaprolactam, e.g. Luviskol® Plus (BASF SE), and polyvinylpyrrolidone and copolymers of these, in particular with vinyl esters, for example vinyl acetate, e.g. Luviskol® VA 37, VA 55, VA 64, VA 73 (BASF SE); polyamides, e.g. those based on itaconic acid and on aliphatic diamines and described by way of example in DE-A-43 33 238.

Other suitable polymers are amphoteric or zwitterionic polymers, for example the octylacrylamide/methyl methacrylate/tert-butylaminoethyl methacrylate/2-hydroxypropyl methacrylate copolymers obtainable as Amphomer® (National Starch), and also the zwitterionic polymers disclosed by way of example in the German patent applications DE 39 29 973, DE 21 50 557, DE 28 17 369 and DE 37 08 451. Acrylamidopropyltrimethylammonium chloride/(meth) acrylic acid copolymers and their alkali metal and ammonium salts are preferred zwitterionic polymers. Other suitable zwitterionic polymers are methacroylethylbetaine/methacrylate copolymers, obtainable commercially as Amersette® (AMERCHOL), and copolymers of hydroxyethyl methacrylate, methyl methacrylate, N,N-dimethylaminoethyl methacrylate and acrylic acid (Jordapon®).

Other suitable polymers are nonionic, siloxane-containing, water-soluble or -dispersible polymers, e.g. polyethersiloxanes, for example Tegopren® (Goldschmidt) and Belsil® (Wacker).

In a specific embodiment, the compositions of the invention comprise at least one polymer which acts as thickener.

Examples of suitable polymeric thickeners are optionally modified polymeric natural substances (carboxymethylcellulose and other cellulose ethers, hydroxyethyl- and -propylcellulose and the like), and also synthetic polymeric thickeners (polyacrylic and polymethacrylic compounds, vinyl polymers, polycarboxylic acids, polyethers, polyimines, polyamides). Among these are the polyacrylic and polymethacrylic compounds that have to some extent already been mentioned above, for example the high-molecular-weight homopolymers of acrylic acid crosslinked with a polyalkenyl polyether, in particular with an allyl ether of sucrose, pentaerythritol or propylene (INCI name: carbomer). These polyacrylic acids are obtainable inter alia from BF Goodrich with trademark Carbopol®, e.g. Carbopol 940 (molecular weight about 4 000 000), Carbopol 941 (molecular weight ca. 1 250 000) or Carbopol 934 (molecular weight about 3 000 000). These materials also include acrylic acid copolymers which are obtainable by way of example from Rohm & Haas with the trademarks Aculyn® and Acusol®, e.g. the anionic, nonassociative polymers Aculyn 22, Aculyne 28, Aculyn 33 (crosslinked), Acusol 810, Acusol 823 and Acusol 830 (CAS 25852-37-3). Other especially suitable materials are associative thickeners, e.g. those based on modified polyurethanes (HEUR) and hydrophobic modified acrylic or (meth)acrylic acid copolymers (HASE (high alkali swellable emulsion) thickeners).

In a preferred embodiment, the compositions of the invention are skin cleansers.

Preferred skin cleansers are soaps of liquid to gel-type consistency, for example transparent soaps, luxury soaps, deodorant soaps, cream soaps, baby soaps, skin-protection soaps, abrasive soaps and syndets, paste-type soaps, soft soaps and washing pastes, liquid washing, shower and bath preparations, for example washing lotions, shower baths and shower gels, bubble baths, oil baths and scrub preparations, shaving foams, shaving lotions and shaving creams.

Skin cleansers preferably comprise a proportion, based on the total weight of the cleanser, of about 0.001 to 70% by weight, preferably from 0.01 to 50% by weight, very particularly preferably from 0.1 to 30% by weight, of at least one compound of the formula (I) and of the formula (I').

In another preferred embodiment, the compositions of the invention involve a shower gel, a shampoo formulation or a bath preparation.

These formulations comprise at least one compound of the general formula (I) or (I') as main surfactant and optionally at least one amphoteric and/or nonionic surfactant as cosurfactant. Other suitable active ingredients and/or auxiliaries are generally selected from lipids, fragrances, dyes, organic acids, preservatives, antioxidants, thickeners/gelformers, skin conditioners and humectants.

These formulations preferably comprise, based on the total weight of the formulation, from 2 to 50% by weight, preferably from 5 to 40% by weight, particularly preferably from 8 to 30% by weight, of surfactants.

The washing preparations, shower preparations and bath preparations can also use any of the anionic, neutral, amphoteric or cationic surfactants usually used in body-cleaning compositions.

Suitable surfactants are the abovementioned.

The shower-gel/shampoo formulations can moreover comprise additional thickeners, for example sodium chloride, PEG-55, propyleneglycol oleate, PEG-120-methylglucose dioleate and others. Examples of suitable other thickeners commercially obtainable are Arlypon TT (INCI: PEG/PPG-120/10 trimethylolpropane trioleate (and) laureth-2) and Arlypon F (INCI: laureth-2). The shower-gel/shampoo formulations can moreover comprise preservatives, other active ingredients and auxiliaries and water.

The compounds of the formula (I) and of the formula (I') of the invention are also advantageously suitable as surfactants for shampoo formulations which can also comprise other conventional surfactants.

The shampoo formulations can use conventional conditioners in order to achieve certain effects. Among these are by way of example the abovementioned cationic polymers with the INCI name polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10) and acrylamidocopolymers (polyquaternium-7). It is moreover possible to use protein hydrolysates, and also conditioning substances based on silicone compounds, for example polyalkylsiloxanes, polyarylsiloxanes, polyarylalkylsiloxanes, polyether siloxanes or silicone resins. Other suitable silicone compounds are dimethicone copolyols (CTFA) and amino-functional silicone compounds, for example amodimethicone (CTFA). It is moreover possible to use cationic guar derivatives, for example guar hydroxypropyltrimonium chloride (INCI).

In another preferred embodiment, compositions of the invention involve cosmetic compositions for the care and protection of the skin, nail-care compositions or preparations for decorative cosmetics.

The compounds of the formula (I) and of the formula (I') can moreover be used in nose strips for pore cleansing, in anti-acne compositions, repellents, shaving compositions, hair-removal compositions, intimate-care compositions, foot-care compositions, and also in baby-care.

The skin-cosmetic preparations can also comprise, alongside the compounds of the formula (I) and of the formula (I') and suitable carriers, other active ingredients and auxiliaries, as described above, that are conventional in skin cosmetics.

Preferred oil components and fatty components of the skin-cosmetic and dermatological compositions are mineral and synthetic oils, e.g. paraffins, silicone oils and aliphatic hydrocarbons having more than 8 carbon atoms, animal and vegetable oils, e.g. sunflower oil, coconut oil, avocado oil, olive oil, lanolin, and waxes, fatty acids, fatty acid esters, e.g. triglycerides of $C_6$-$C_{30}$-fatty acids, wax esters, e.g. jojoba oil, fatty alcohols, Vaseline, hydrogenation lanolin and acetylated lanolin, and also mixtures thereof.

The skin-cosmetic and dermatological preparations can also comprise conditioning substances based on silicone compounds in order to establish certain properties, e.g. improved haptic properties, spreading behavior, water-resistance and/or the binding of active ingredients and auxiliaries, for example pigments. Examples of suitable silicone compounds are polyalkylsiloxanes, polyarylsiloxanes, polyarylalkylsiloxanes, polyether siloxanes and silicone resins.

Cosmetic or dermatological preparations which comprise at least one compound of the formula (I) or of the formula (I') are produced by conventional processes known to the person skilled in the art.

The cosmetic and dermatological compositions thereby preferably take the form of emulsions, in particular water-in-oil (W/O) or oil-in-water (O/W) emulsions. However, it is also possible to select other types of formulation, examples being hydrodispersions, gels, oils, oleogels, multiple emulsions, for example in the form of W/O/W or O/W/O emulsions, anhydrous salves, or salve bases, etc.

The emulsions are produced by known methods. The emulsions generally comprise, alongside at least one compound of the formula (I) or of the formula (I'), conventional constituents such as fatty alcohols, fatty acid esters and in particular fatty acid triglycerides, fatty acids, lanolin and derivatives thereof, natural or synthetic oils or waxes and emulsifiers in the presence of water. The selection of the emulsion-type-specific additions and the production of suitable emulsions is described by way of example in Schrader, Grundlagen und Rezepturen der Kosmetika [Principles and formulations of cosmetics], Hüthig Buch Verlag, Heidelberg, 2nd edn., 1989, third part, which are hereby expressly incorporated by way of reference.

Preferred fatty components which can be comprised in the fat phase of the emulsions are: hydrocarbon oils, for example paraffin oil, purcellin oil, perhydrosqualene and solutions of microcrystalline waxes in these oils; animal or vegetable oils, for example sweet almond oil, avocado oil, calophylum oil, lanolin and derivatives thereof, castor oil, sesame oil, olive oil, jojoba oil, karite oil, hoplostethus oil; mineral oils which begin to distill at about 250° C. at atmospheric pressure and which had a distillation end point of 410° C., e.g. Vaseline oil; esters of saturated or unsaturated fatty acids, for example alkyl myristates, e.g. isopropyl, butyl or cetyl myristate, hexadecyl stearate, ethyl or isopropyl palmitate, octanoic or decanoic acid triglycerides and cetyl ricinoleate.

The fat phase can also comprise silicone oils which are soluble in other oils and an example of which is dimethylpolysiloxane or methylphenylpolysiloxane, or the silicone-glycol copolymer, fatty acids and fatty alcohols.

It is also possible to use waxes, e.g. carnauba wax, candililla wax, beeswax, microcrystalline wax, ozokerite wax, and the oleates myristates, linoleates and stearates of Ca, Mg and Al.

An emulsion of the invention can moreover take the form of O/W emulsion. This type of emulsion usually comprises an oil phase, emulsifiers which stabilize the oil phase in the aqueous phase, and an aqueous phase which has usually been thickened. Emulsifiers that can be used are preferably O/W emulsifiers such as polyglycerol esters, sorbitan esters or partially esterified glycerides.

In another preferred embodiment, the compositions of the invention involve a hair-treatment composition.

Hair-treatment compositions of the invention preferably comprise a quantity, based on the total weight of the composition, in the range of about 0.1 to 30% by weight, preferably 0.5 to 20% by weight, of at least one compound of the general formula (I) or (I').

The compounds of the formula (I) and of the formula (I') of the invention are also suitable for styling gels. Gel-formers used can be any of the gel-formers conventionally used in cosmetics. In this connection, reference is made to the abovementioned conventional thickeners.

The compounds of the formula (I) and of the formula (I') of the invention are equally suitable for the production of pharmaceutical compositions.

Suitable pharmaceutical auxiliaries are the auxiliaries listed in relevant Pharmacopeias (e.g. DAB, Ph. Eur., BP, NF), and also other auxiliaries having properties suitable for physiological use. These substances are also described by way of example in Fiedler, H. P. Lexikon der Hilfsstoffe für Pharmazie, Kosmetik und angrenzende Gebiete [Encyclopedia of auxiliaries for pharmacy, cosmetics and related sectors] 4th edn., Aulendorf: ECV-Editio-Kantor-Verlag, 1996.

Detergents and Cleaners

The compounds of the formula (I) and of the formula (I') of the invention are also suitable for the production of detergents or cleaners, e.g. for the cleaning of textile fabrics and/or hard surfaces. These cleaners can take the form of a dishwashing composition for manual or machine use, of all-purpose cleaner for non-textile surfaces, e.g. made of metal, or made of coated wood or plastic, or may take the form of cleaning compositions for ceramic products, for example porcelain or tiles. It is preferable that the detergents or cleaners of the invention take the form of a liquid textile detergent. Said compositions can also, if desired, be formulated as pigments.

Examples of other formulations in which at least one compound of the general formula (I) or of the formula (I') as defined above can advantageously be used are
- crop-protection compositions,
- wetting agents,
- thickeners,
- coating materials, coating compositions, adhesives, leather-treatment compositions or textile-treatment compositions or paper-treatment materials, and/or
- chemicals for tertiary mineral oil production.

Examples of other formulations in which at least one compound of the general formula (I) or of the formula (I') as defined above can advantageously be used are
- all-purpose cleaners, spray cleaners and hand-dishwashing compositions for cleaning in the private, industrial and institutional sector;
- humectants;
- printing-roll- and printing-plate-cleaning compositions in the printing industry;
- formulations for spray applications, for example in inkjet inks;
- compositions for metal-treatment, for example corrosion-protection formulations;
- cutting, grinding or drilling aids and lubricants;
- formulations in the textile industry, for example leveling agents or formulations for yard cleaning;
- flotation aids and foaming aids.

These formulations usually comprise other ingredients such as surfactants, builders, fragrances and dyes, complexing agents, polymers and other ingredients.

The compounds of the general formula (I) of the invention can generally be used in any of the sectors requiring a thickening effect active at interfaces. The compounds of the general formula (I) are moreover suitable for improving the solubility of other components, e.g. of other surface-active components, for example of anionic surfactants. They therefore also contribute favorably to the formation of clear surfactant-containing solutions.

EXAMPLES

The process is explained in more detail via the examples below.

Surface tension is measured as described in DIN EN 14370.

Example 1

84.5 g of sodium lactate, 0.5 g of KOtBu and 200 ml of xylene are used as initial charge at 80° C. in an autoclave. The autoclave is inertized with nitrogen. The vacuum is then relieved with nitrogen and the temperature is increased up to 90° C. 166 g of ethylene oxide are added at this temperature within a period of 4 h. The mixture is then stirred at this temperature for a further 10 h. All of the volatile constituents are removed in vacuo.

This gives 229.0 g of a brown viscose substance.
Saponification value: 0 mg KOH/g
IR: 1599 cm$^{-1}$ Example 2

76.1 g of sodium lactate, 0.6 g of KOtBu and 250 ml of xylene are used as initial charge at 80° C. in an autoclave. The autoclave is inertized with nitrogen. The vacuum is then relieved with nitrogen and the temperature is increased up to 120° C. 74.7 g of ethylene oxide are added at this temperature within a period of 1 h. The mixture is then stirred at this temperature for a further 6 h. 124.9 g of dodecene epoxide are then added within a period of 2 h. The mixture is then stirred at this temperature for a further 12 h. All of the volatile constituents are removed in vacuo. After removal of the solvent, this gives 270.0 g of a brown viscose substance.
Saponification value: 0.7 mg KOH/g
IR: 1599 cm$^{-1}$
Surface tension: 27.4 mN/m (1 g/l, 25° C.)

Example 3

0.1 g of KOtBu is added to 87.4 g of the product of example 1. 48.4 g of dodecene epoxide are added dropwise within a period of 10 min under a stream of nitrogen and at a temperature of 50° C. The temperature is then increased to 90° C. and the mixture is stirred at this temperature for a further 6 h. This gives 134.0 g of a brown solid.
Surface tension: 30.5 mN/m (1 g/l, 25° C.)

Example 4

15.6 g of hexadecene epoxide are added dropwise within a period of 10 min to 22.1 g of the product of example 1 under a stream of nitrogen and at a temperature of 90° C. The mixture is then stirred at this temperature for a further 14 h. This gives 134.0 g of a brown solid.
IR: 1600 cm$^{-1}$ Example 5

129.0 g of sodium salt of 12-hydroxystearic acid, 0.4 g of KOtBu and 800 ml of xylene are used as initial charge at 80° C. in an autoclave. The autoclave is inertized with nitrogen. The vacuum is then relieved with nitrogen and the temperature is increased up to 120° C. 86.9 g of ethylene oxide are added at this temperature within a period of 1.5 h. The mixture is then stirred at this temperature for a further 10 h. All of the volatile constituents are removed in vacuo. This gives 201.0 g of a beige solid.
Saponification value: 0 mg KOH/g
IR: 1561 cm$^{-1}$ Example 6

373.5 g of sodium ricinoleate, 1.2 g of KOtBu and 1000 ml of xylene are used as initial charge at 80° C. in an autoclave. The autoclave is inertized with nitrogen. The vacuum is then relieved with nitrogen and the temperature is increased up to 120° C. 220.0 g of ethylene oxide are added at this temperature within a period of 5 h. The mixture is then stirred at this temperature for a further 10 h. All of the volatile constituents are removed in vacuo. This gives 580.0 g of a beige solid.
Saponification value: 2.6 mg KOH/g
IR: 1557 cm$^{-1}$ Comparative Example 90.7 g of lactic acid (99.3%) and 0.54 g of KOH (50% in H$_2$O) are used as initial charge at 80° C. in an autoclave. The autoclave is inertized with nitrogen. The mixture is then stirred in vacuo (<10 mbar) for 2 h at 80° C. The vacuum is then relieved with nitrogen and the temperature is increased up to 90° C. 44.0 g of ethylene oxide are added at this temperature within a period of 10 min, and the mixture is then stirred at this temperature for a further 5 h. All of the volatile constituents are then removed in vacuo. This gives 134 g of a clear pale liquid.

Acid value: 6.4 mg KOH/g
Saponification value: 433.9 mg KOH/g
IR: 1734 cm$^{-1}$

The invention claimed is:
1. A compound of the formula I'

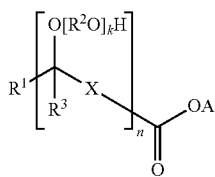
(I')

in which
R$^1$ is selected from the group consisting of C$_1$-C$_{10}$ alkyl, a branched saturated or unsaturated aliphatic hydrocarbon moiety having from 1 to 30 carbon atoms, a linear unsaturated aliphatic hydrocarbon moiety having from 1 to 30 carbon atoms, saturated or unsaturated cycloaliphatic hydrocarbon moieties having from 3 to 10 carbon atoms, and aryl,
R$^3$ is selected from the group consisting of hydrogen and methyl,
R$^2$ is —CR$^a$R$^b$—CR$^c$R$^d$—, in which each R$^a$, R$^b$, R$^c$ and R$^d$ is mutually independently selected from the group consisting of hydrogen, unsubstituted C$_1$-C$_{30}$-alkyl and unsubstituted C$_5$-C$_7$-cycloalkyl and C$_5$-C$_7$-cycloalkyl which bears 1, 2 or 3 substituents mutually independently selected from C$_1$-C$_6$-alkyl and C$_2$-C$_6$-alkenyl, where two moieties R$^a$ and R$^c$, together with the —CR$^b$—CR$^d$— group to which they are bonded, can also be C$_5$-C$_7$-cycloalkyl which is unsubstituted or which bears 1, 2 or 3 substituents mutually independently selected from the group consisting of C$_1$-C$_6$-alkyl and C$_2$-C$_6$-alkenyl;
X is respectively a bond or a divalent linear or branched saturated or unsaturated aliphatic hydrocarbon moiety having from 1 to 30 carbon atoms, or a divalent saturated or unsaturated cycloaliphatic hydrocarbon moiety having from 3 to 10 carbon atoms;
n is a number from 1 to 10;
k is a number from 2 to 100; and
A is hydrogen or one cation equivalent,
2-[2-(2-hydroxyethoxy)ethoxy]propanoic acid being excluded.

2. The compound according to claim 1, in which R$^2$ is —CHR$^a$—CHR$^c$—, in which each R$^a$ is independently selected from the group consisting of hydrogen, unsubstituted C$_1$-C$_{20}$-alkyl, unsubstituted C$_5$-C$_7$-cycloalkyl, C$_5$-C$_7$-cycloalkyl having 1, 2 or 3 C$_1$-C$_6$-alkyl substituents, and each R$^c$ is respectively independently selected from the group consisting of hydrogen and methyl.

3. The compound according to claim 1, in which A is hydrogen, an alkali metal cation or one equivalent of an alkaline earth metal cation.

4. The compound according to claim 1, in which k is a number from 2 to 50.

5. The compound (I') according to claim 1, in which R$^1$ is selected from the group consisting of C$_2$-C$_{25}$-alkenyl and phenyl.

6. The compound (I') according to claim 1, where R$^1$ is methyl, ethyl, n-propyl, isopropyl, n-butyl, isobutyl, sec-butyl, tert-butyl, n-pentyl, isoamyl, n-hexyl, 2-ethylhexyl, n-heptyl, n-octyl, n-nonyl, n-decyl, 2-propylheptyl, isotridecyl, isostearyl, oleyl, linoleyl, or-linolenyl.

7. The compound (I') according to claim 1, in which X is selected from the group consisting of a bond, C$_1$-C$_{20}$-alkylene, and C$_2$-C$_{20}$-alkenylene.

8. The compound (I') according to claim 1, in which R$^3$ is hydrogen.

9. The compound (I') according to claim 1, in which n is 1 or 2.

10. A process for the production of compounds of the general formula (I') as defined in claim 1, wherein
at least one hydroxycarboxylic salt of the formula III'

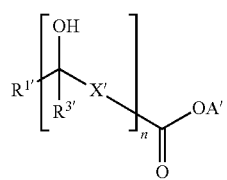
(III')

in which
R$^{1'}$ is selected from the group consisting of C$_1$-C$_{10}$ alkyl, a branched saturated or unsaturated aliphatic hydrocarbon moiety having from 1 to 30 carbon atoms, a linear unsaturated aliphatic hydrocarbon moiety having from 1 to 30 carbon atoms, saturated or unsaturated cycloaliphatic hydrocarbon moieties having from 3 to 10 carbon atoms, and aryl;
R$^{3'}$ is selected from the group consisting of hydrogen and methyl;
X' is respectively a bond or a divalent linear or branched saturated or unsaturated aliphatic hydrocarbon moiety having from 1 to 30 carbon atoms, or a divalent saturated or unsaturated cycloaliphatic hydrocarbon moiety having from 3 to 10 carbon atoms;
n has is a number from 1 to 10; and
A' is one cation equivalent,
is reacted with at least one epoxide of the general formula (IV)

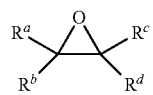
(IV)

in which
each R$^a$, R$^b$, R$^c$ and R$^d$ is mutually independently selected from the group consisting of hydrogen, unsubstituted C$_1$-C$_{30}$-alkyl and unsubstituted C$_5$-C$_7$-cycloalkyl and C$_5$-C$_7$-cycloalkyl which bears 1, 2 or 3 substituents which are mutually independently selected from the group consisting of C$_1$-C$_6$-alkyl and C$_2$-C$_6$-alkenyl, where two moieties $R^a$ and $R^c$, together with the $-CR^b-CR^d-$ group to which they are bonded, can also be $C_5$-$C_7$-cycloalkyl which is unsubstituted or bears 1, 2 or 3 substituents mutually independently selected from the group consisting of $C_1$-$C_6$-alkyl and $C_2$-$C_6$-alkenyl; and b) the reaction product from step a) is optionally treated with an acid.

11. The process according to claim 10, where the hydroxycarboxylic salt is selected from the group consisting of salts of lactic acid, 12-hydroxystearic acid, ricinoleic acid, 3-hydroxybutyric acid, mandelic acid and mixtures thereof.

12. The process according to claim 10, wherein the alkylene oxide is selected from the group consisting of ethylene oxide, propylene oxide, 1,2-butylene oxide, 2,3-butylene oxide, $C_{10}$-$C_{30}$-alkylene oxides and mixtures thereof.

13. The process according to claim 12, where the reaction in step a) uses at least two different alkylene oxides.

14. A compound of the formula (I') obtainable via a process as defined in claim 10.

15. The compound according to claim 4, in which k is a number from 2 to 20.

16. The compound according to claim 15, in which k is a number from 2 to 10.

17. A composition comprising the compound of Formula I' of claim 1, wherein the composition is a formulation of
cosmetic compositions,
pharmaceutical compositions,
detergents and cleaners,
crop-protection compositions,
wetting agents,
thickeners,
coating materials, coating compositions, adhesives, leather-treatment compositions or textile-treatment compositions, and/or
chemicals for tertiary mineral oil production.

* * * * *